United States Patent [19]

Schultz

[11] Patent Number: 5,292,248
[45] Date of Patent: Mar. 8, 1994

[54] MOLAR APPLIANCE

[75] Inventor: Charles J. Schultz, West Babylon, N.Y.

[73] Assignee: GAC International, Inc., Central Islip, N.Y.

[21] Appl. No.: 956,825

[22] Filed: Oct. 5, 1992

Related U.S. Application Data

[63] Continuation of Ser. No. 782,371, Oct. 24, 1991, abandoned.

[51] Int. Cl.⁵ .............................................. A61C 3/00
[52] U.S. Cl. .................................... 433/17; 433/8
[58] Field of Search ............................ 433/17, 5

[56] References Cited

U.S. PATENT DOCUMENTS

| | | | |
|---|---|---|---|
| 3,660,900 | 5/1972 | Andrews | 433/24 |
| 4,741,696 | 5/1988 | Cetlin | 433/7 |
| 4,781,582 | 11/1988 | Kesling | 433/17 |
| 4,820,151 | 4/1989 | Pospisil | 433/17 |
| 4,886,451 | 12/1989 | Cetlin | 433/7 |
| 4,963,092 | 10/1990 | Snead | 433/17 |
| 5,057,012 | 10/1991 | Kesling | 433/5 |
| 5,059,119 | 10/1991 | Snead | 433/17 |

OTHER PUBLICATIONS

Catalog 1990, TP Orthodontics, Inc., Copyright 1990 TP Orthodontics, Inc. (p. 44).

*Primary Examiner*—John J. Wilson
*Attorney, Agent, or Firm*—Kenyon & Kenyon

[57] ABSTRACT

An orthodontic appliance has a tooth-abutting surface oriented at an acute angle relative to the base of an arch-wire slot. A lip bumper tube of the appliance is reverse offset relative to the base of the arch-wire slot to obtain more accurate manipulation of the force and torque vectors applied to the tooth. The angle of the base also reduces occlusal interference by gingivally inclining the lip bumper. Wedge-shaped occlusal tie wings further reduce occlusal interference. An auxiliary hook of the appliance is shaped so that its extension in the buccal direction is less than that of the lip bumper tube to reduce patient irritation and discomfort.

16 Claims, 2 Drawing Sheets

MOLAR APPLIANCE

This application is a continuation of application Ser. No. 07/782,371, filed on Oct. 24, 1991, now abandoned.

FIELD OF THE INVENTION

The present invention relates to orthodontic appliances for correcting abnormal tooth alignment, and more particularly, to an improvement in orthodontic appliances for applying a system of force and torque vectors to molar teeth to achieve normal alignment.

BACKGROUND OF THE INVENTION

Typical known molar appliances are shown, for example, in U.S. Pat. Nos. 4,886,451, and 4,820,151. Patient discomfort and irritation has often been associated with many known molar appliances. Irritation is typically attributable to hooks that provide anchorage for ligature or elastics protruding from the appliances. The hooks frequently rub against the inner surface of a patient's cheek causing irritation. It has also proven to be difficult to accurately set up the desired configuration of force vectors applied by the appliance to the teeth. Using one known method, torque is applied to the tooth by twisting the archwire. This method, however, is relatively inaccurate, time consuming, and depends to a large extent on the individual skill of the orthodontist. A more recent improvement on this method involves the application of torque to the tooth through the angulation of the arch-wire slot. An arch wire is inserted into an arch-wire slot oriented at an acute angle relative to the surface of the tooth, however, because the torque is applied by the arch-wire slot, the point of application of the torque is more in occlusion than is typically desired. It has also been found at times to be difficult to accurately place the appliance on the tooth because the angled orientation of the arch-wire slot can be visually confusing.

SUMMARY OF THE INVENTION

The present invention is directed to an orthodontic appliance comprising a base portion defining an arch-wire slot formed by a base surface and two side walls located on either side of the base surface for receiving an arch wire. The appliance further comprises a tooth-abutting surface shaped to conform to the surface of a tooth for attachment to the surface of the tooth. The tooth-abutting surface is oriented at an acute angle relative to a plane of the base surface of the arch-wire slot for applying a torque to the tooth through the tooth-abutting surface. A lip-bumper portion is coupled to the base portion and defines a lip-bumper tube for receiving a lip bumper. An occlusal surface of the lip-bumper portion is oriented in a plane substantially parallel to the plane of the base surface of the arch-wire slot to facilitate visual alignment of the appliance on the tooth. A hook portion is located on the opposite side of the arch-wire slot relative to the lip-bumper portion for attaching an elastic or auxiliary appliance.

One orthodontic appliance of the present invention further comprises at least one first tie wing extending gingivally from the base portion and supporting the hook portion. At least one second tie wing is located on the opposite side of the arch-wire slot relative to the first tie wing and is coupled to the lip-bumper portion. The first and second tie wings preferably each define a substantially wedge-shaped portion to facilitate the attachment of an elastic or ligature to the respective appliance.

One orthodontic appliance of the present invention comprises two first tie wings extending gingivally from the base portion and spaced apart from each other, and at least one of the first tie wings supports the hook portion. In another orthodontic appliance of the present invention, the acute angle of the tooth-abutting surface relative to a plane of the base surface of the arch-wire slot is approximately 25°.

One advantage of the appliance of the present invention is that the tooth-abutting surface is oriented at an acute angle relative to a plane of the base surface of the arch-wire slot. As a result, the torque is applied to the tooth through the base of the appliance. Accordingly, a greater placement accuracy, and greater control over the force vectors applied to the tooth can thus be obtained. In addition, by applying torque with the tooth-abutting surface of the appliance, the lip bumper portion is angled toward the gingival, and thus away from occlusal interference.

Other advantages of the present invention will be readily appreciated as the invention becomes better understood by reference to the following detailed description when considered in conjunction with the accompanying drawings.

DETAILED DESCRIPTION

Figure 1:
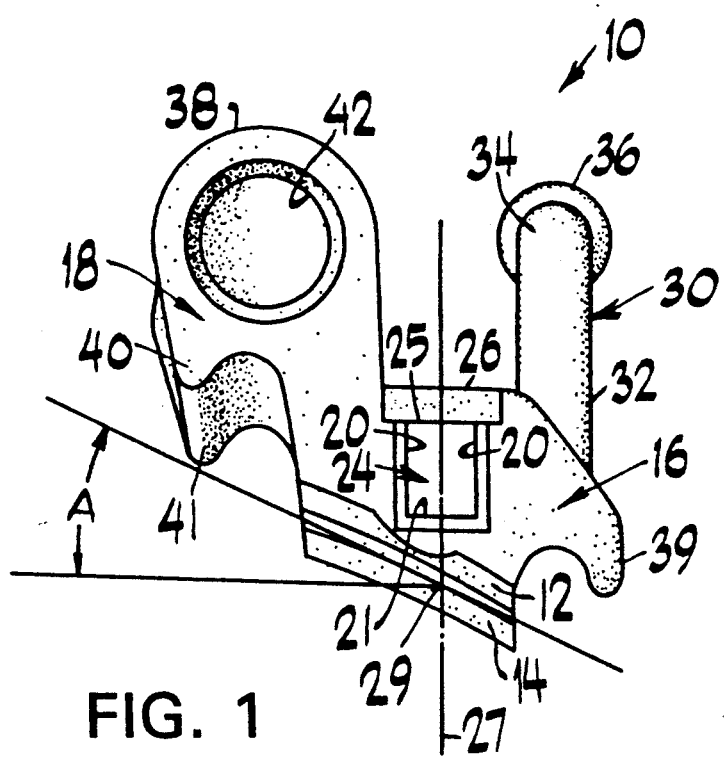
FIG. 1 is a front (mesial) plan view of a molar appliance embodying the present invention.
Figure 2:
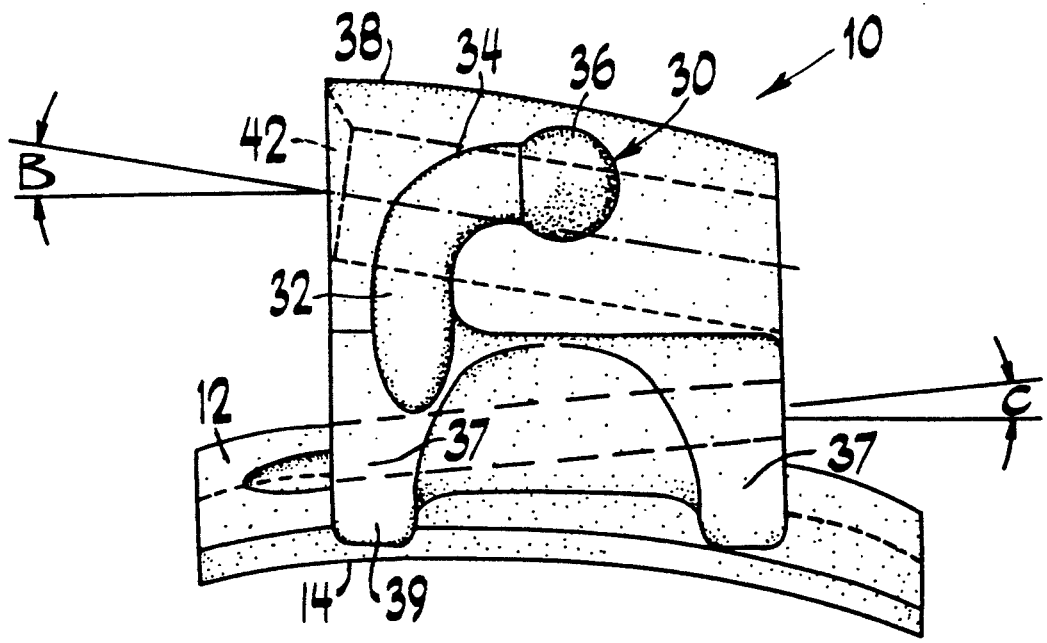
FIG. 2 is a side plan view of the appliance of FIG. 1.
Figure 3:
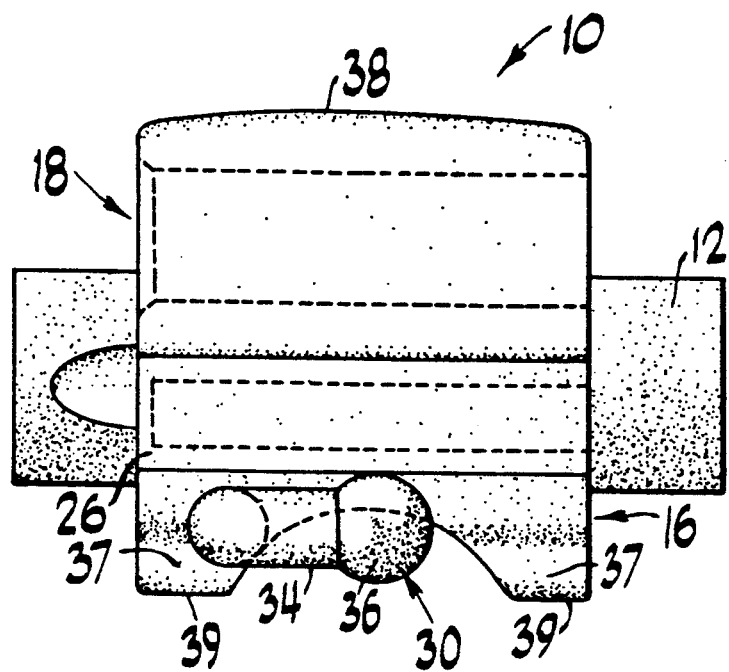
FIG. 3 is a top plan view of the appliance of FIG. 1.

In FIGS. 1-4 a molar appliance embodying the present invention is indicated generally by the reference numeral 10. As sown in FIGS. 1 and 2, the appliance 10 includes a base 12, which defines a tooth-abutting surface 14. As shown in FIG. 2, the tooth-abutting surface 14 is contoured to conform to the curvature of a tooth for attaching the appliance 10 to a tooth. The tooth-abutting surface 14 can be attached to a tooth by means of a molar band (not shown), for example. A bracket body extends buccally from the base 12 and defines occlusal and gingival portions indicated by the numerals 16 and 18, respectively, as shown in FIG. 1. A rectangular arch-wire slot 24 is formed in the base 12 for receiving an arch wire (not shown) and extends across the buccal side of the appliance in the mesial-distal direction, thus forming a divider between the occlusal portion 16 and gingival portion 18, as shown in FIG. 3. The arch-wire slot 24 is defined by parallel side walls 20 and a base wall 21, as shown in FIG. 1. A recessed portion 25 is formed along the buccal edges of the arch-wire slot 24 and is dimensioned to receive an arch-wire cap 26 for retaining the arch wire upon insertion of the arch wire into the arch-wire slot 24.

In FIG. 1, a line 27 is illustrated which is normal to the base wall 21 of the arch-wire slot 24 and intersects the tooth-abutting surface 14 at a point 29. In accordance with the present invention, the tooth-abutting surface 14 is oriented so that a line tangent to its surface a point 29 intersects a plane parallel to the base wall 21 of the arch-wire slot 24 at an angle A, as shown in FIG. 1. The angle A is less than 90°, and in the embodiment of the present invention illustrated it is preferably approximately 25°. Accordingly, when the appliance 10 is mounted to a tooth, a torque is applied through the tooth-abutting surface 14 to the tooth. One advantage of the appliance of the present invention over prior molar appliances in which torque is cut into the arch-wire slot (i.e., the arch-wire slot is cut an angle relative to the tooth-abutting surface), is that the surface applying the torque is in immediate contact with the tooth and is therefore less in occlusion than such prior appliances with torque cut into the arch-wire slot. Thus, the appliance of the present invention can typically more accurately apply the desired torque to the tooth. Another advantage of the appliance of the present invention is that the angular orientation of the tooth-abutting surface 14 angles the appliance 10 away from occlusal interference upon mounting to a tooth, and thus further enhances patient comfort.

Figure 4:
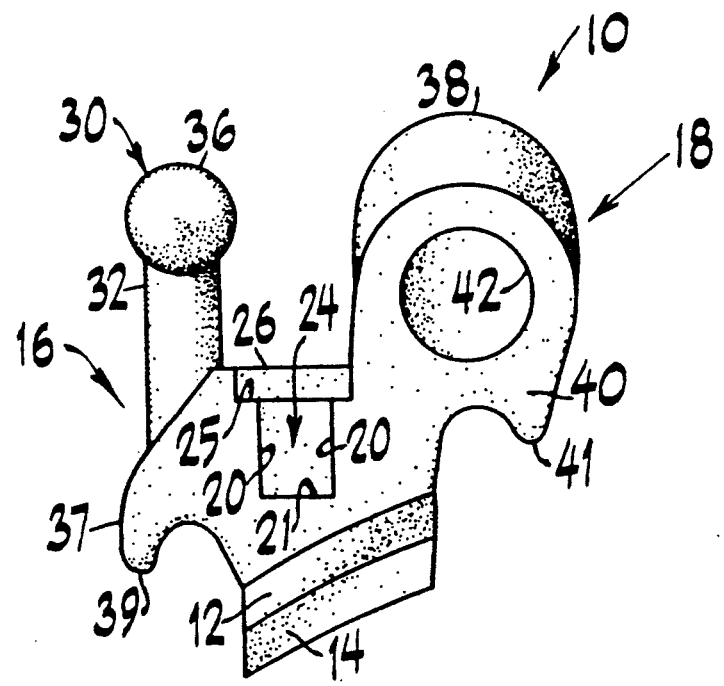
FIG. 4 is a rear (distal) plan view of the appliance of FIG. 1.

A distally-opening hook 30 projects outwardly from the occlusal portion 16 and includes a base 32 and an arm 34, as shown for example in FIG. 2. A ball 36 is defined on the end of the arm 34 and has a slightly greater diameter than the rest of the arm 34. The distally-opening hook 30 provides the additional advantages of greater patient comfort because of its rounded configuration, the relative ease of attaching elastics, the ability to retain such elastics attached by the patient, and the ability to hold eyelets for coil springs for applying an auxiliary force through the appliance. As will be recognized by those skilled in the art, the combination of these advantages will make the regular use of the appliance of the present invention more acceptable to patients and clinicians The occlusal portion 16 also includes mesial and distal wedge-shaped tie wings 37. Each wedge-shaped tie wing 37 defines a tip portion 39 for wrapping a ligature or otherwise securing an elastic to the respective tie wing 37. The gingival portion 18 defines a lip-bumper portion 38, which in turn defines a single tie-wing portion 40. As shown in FIGS. 1 and 4, the single tie-wing portion 40 is formed with a wedge shape similar to the wedge shape of the tie wings 37, and includes a tip portion 41 for wrapping a ligature or otherwise securing an elastic member to the tie-wing portion 40. The wedge shape of the tie-wings 37 and single tie-wing portion 40 further prevents occlusal interference when the appliance 10 is mounted to a tooth, and thus enhances patient comfort. The lip-bumper portion 38 further defines a lip-bumper tube 42 for receiving a lip-bumper (not shown). As shown in FIG. 1, the lip-bumper portion 38 extends a greater distance in the buccal direction than does the distally-opening hook 30, thus preventing the distally-opening hook 30 from causing buccal irritation. Also, because the torque is in the tooth-abutting surface of the appliance of the present invention (as opposed to being cut into the arch-wire slot), the occlusal surface of the lip-bumper portion 38 is oriented in a plane substantially parallel to the base surface 21 of the arch-wire slot 24, thus facilitating visual alignment of the appliance on a tooth.

As shown in FIG. 2, the longitudinal axis of the lip-bumper tube 42 is offset in the mesial direction with respect to the mesial-distal axis by an angle B. The arch-wire slot 24, on the other hand, is offset in the distal direction with respect to the mesial-distal axis by an angle C. In the embodiment of the present invention illustrated, the angle B is preferably approximately 5°, and the angle C is preferably approximately 4°. The appliance 10 therefore has a reverse offset, i.e., the lip-bumper tube 42 is mesially offset by an angle B, and the arch-wire slot 24 is distally offset by an angle C. Thus, one advantage of the appliance of the present invention is that the mesially-offset lip bumper tube 42 facilitates the insertion of a lip bumper at an early stage of treatment.

As shown in FIG. 3, the distally-opening hook 30 does not extend in the occlusal direction further than does the wedge-shaped tie wings 37, thus preventing any occlusal interference, which is typically associated with hooks on prior orthodontic appliances. Also, as shown in FIGS. 2 and 3, the base 12 extends in both the mesial and distal directions beyond the occlusal portion 16 and gingival portion 18, thus providing a greater surface area for the tooth-abutting surface 14.

As shown in FIG. 1, the mesial opening of the arch-wire slot 24 is defined by a chamfered edge 44 and the mesial opening of the lip-bumper tube 42 is similarly defined by a chamfered edge 46, which are each provided to facilitate the insertion of an arch wire and lip bumper, respectively.

I claim:

1. An orthodontic appliance for a molar comprising:
   a gingival portion defining a first tie-wing and a lip-bumper portion defining an opening for receiving a lip bumper, the first tie wing being wedge shaped;
   an occlusal portion defining a second tie-wing, the second tie-wing being wedge shaped;
   an arch-wire slot defining a base surface and extending substantially in the mesial-distal direction between the gingival and occlusal portions for receiving an arch wire;
   a distally-opening hook portion defining a base extending from the occlusal portion in the buccal direction and an arm portion coupled to the base portion extending distally from the base portion; and
   a base defining a tooth-abutting surface and coupled to the occlusal and gingival portions, the tooth-abutting surface being oriented at an acute angle relative to a plane of the base surface of the arch-wire slot for applying a torque to the molar through the tooth-abutting surface.

2. An orthodontic appliance as defined in claim 1, wherein the distally-opening hook portion extends a distance in the buccal direction less than the gingival portion in the buccal direction to prevent buccal irritation by the distally-opening hook portion.

3. An orthodontic appliance as defined in claim 1, wherein the base surface of the arch-wire slot is offset with respect to the mesial-distal axis of the appliance by a first acute angle in the distal direction, and the opening of the lip-bumper portion is offset with respect to the mesial-distal axis of the appliance by a second acute angle in the mesial direction.

4. An orthodontic appliance as defined in claim 3, wherein the first acute angle is approximately 4° and the second acute angle is approximately 5°.

5. An orthodontic appliance as defined in claim 1, wherein a surface defining the opening in the lip bumper portion is chamfered to facilitate insertion of a lip bumper.

6. An orthodontic appliance as defined in claim 1, wherein the surfaces defining the mesial end of the arch-wire slot are chamfered to facilitate insertion of an arch wire.

7. An orthodontic appliance as defined in claim 1, wherein the acute angle of the tooth-abutting surface relative to the plane of the base surface of the arch-wire slot is approximately 25°.

8. An orthodontic appliance comprising:
a base portion defining an arch-wire slot formed by a base surface and two side walls located on either side of the base surface for receiving an arch wire, and further including a tooth-abutting surface oriented at an acute angle relative to a plane of the base surface of the arch-wire slot for applying a torque to the tooth through the tooth-abutting surface;
a lip-bumper portion coupled to the base portion and defining a lip-bumper tube for receiving a lip bumper, an occlusal surface of the lip-bumper portion being oriented in a plane substantially parallel to the plane of the base surface of the arch-wire slot to facilitate visual alignment of the appliance on the tooth;
a hook portion located on the opposite side of the arch-wire slot relative to the lip-bumper portion for attaching an elastic or auxiliary appliance;
at least one first tie wing extending gingivally from the base portion; and
at least one second tie wing located on the opposite side of the arch-wire slot relative to the first tie wing, wherein the first and second tie wings each define a substantially wedge-shaped portion to facilitate the attachment of an elastic or ligature to the respective tie wing.

9. An orthodontic appliance as defined in claim 8, wherein the acute angle of the tooth-abutting surface relative to a plane of the base surface of the arch-wire slot is approximately 25°.

10. An orthodontic appliance as defined in claim 8, wherein an occlusal surface of each of the first and second tie wings is located in a plane substantially parallel to a plane of the base surface of the arch-wire slot to facilitate visual alignment of the appliance on a tooth.

11. An orthodontic appliance as defined in claim 8, wherein a plane of the base surface of the arch-wire slot is distally offset by a first acute angle, and the lip-bumper tube is mesially offset by a second acute angle.

12. An orthodontic appliance as defined in claim 11, wherein the first acute angle is approximately 4° and the second acute angle is approximately 5°.

13. An orthodontic appliance as defined in claim 8, wherein the lip-bumper portion extends further buccally than does the hook portion to prevent buccal irritation by the hook portion.

14. An orthodontic appliance as defined in claim 8, wherein the hook portion includes an arm portion extending substantially in the distal direction and the hook portion includes an enlarged ball portion positioned on the distal end of the arm portion for attaching an elastic or auxiliary appliance.

15. An orthodontic appliance for a molar comprising:
a gingival portion defining a first tie-wing and a lip-bumper portion defining an opening for receiving a lip bumper, the first tie-wing being wedge shaped;
an occlusal portion defining a second tie-wing, the second tie-wing being wedge shaped;
an arch-wire slot defining a base surface and extending substantially in the mesial-distal direction between the gingival and occlusal portions for receiving an arch wire;
a distally-opening hook portion defining a base extending from the occlusal portion in the buccal direction and an arm portion coupled to the base portion extending distally from the base portion, the arm portion including an enlarged end portion having the general shape of a ball; and
a base defining a tooth-abutting surface and coupled to the occlusal and gingival portions, the tooth-abutting surface being oriented at an acute angle relative to a plane of the base surface of the arch-wire slot for applying a torque to the molar through the tooth-abutting surface.

16. An orthodontic appliance comprising:
a base portion defining an arch-wire slot formed by a base surface and two side walls located on either side of the base surface for receiving an arch wire, and further including a tooth-abutting surface oriented at an acute angle relative to a plane of the base surface of the arch-wire slot for applying a torque to the tooth through the tooth-abutting surface;
lip-bumper portion extending gingivally from the base portion and defining a lip-bumper tube for receiving a lip bumper, an occlusal surface of the lip-bumper portion being oriented in a plane substantially parallel to the plane of the base surface of the arch-wire slot to facilitate visual alignment of the appliance on the tooth;
a hook portion located on the opposite side of the arch-wire slot relative to the lip-bumper portion such that the hook portion is located in an occlusal position relative to the arch-wire slot for attaching an elastic or auxiliary appliance; the hook portion including an enlarged end portion having the general shape of a ball;
at least one first tie wing extending in an occlusal direction from the base portion; and
at least one second tie wing located on the opposite side of the arch-wire slot relative to the first tie wing, wherein the first and second tie wings each define a substantially wedge-shaped portion to facilitate the attachment of an elastic or ligature to the respective tie wing.

* * * * *